US006884910B2

(12) United States Patent
Harris

(10) Patent No.: US 6,884,910 B2
(45) Date of Patent: Apr. 26, 2005

(54) USES FOR AMINO ACID ANTICONVULSANTS

(75) Inventor: Robert H. Harris, Holmdel, NJ (US)

(73) Assignee: Research Corporation Technologies, Inc., Tucson, AZ (US)

(*) Notice: Subject to any disclaimer, the term of this patent is extended or adjusted under 35 U.S.C. 154(b) by 269 days.

(21) Appl. No.: 09/938,677

(22) Filed: Aug. 24, 2001

(65) Prior Publication Data

US 2002/0086828 A1 Jul. 4, 2002

Related U.S. Application Data

(60) Provisional application No. 60/228,230, filed on Aug. 25, 2000.

(51) Int. Cl.$^7$ .............................................. C07C 229/04
(52) U.S. Cl. ...................... 562/553; 562/567; 562/575
(58) Field of Search ................................ 562/553, 567, 562/575; 514/17–19; 530/330, 331

(56) References Cited

U.S. PATENT DOCUMENTS

| | | | | |
|---|---|---|---|---|
| 4,510,082 A | * | 4/1985 | Gesellchen et al. ......... | 530/302 |
| 4,518,587 A | * | 5/1985 | Laruelle et al. ............ | 514/19 |
| 4,533,657 A | * | 8/1985 | Morgan ..................... | 514/19 |
| 4,707,468 A | * | 11/1987 | Yoshino et al. ............ | 514/16 |
| 5,378,729 A | | 1/1995 | Kohn et al. ............. | 514/231.2 |
| 5,508,266 A | * | 4/1996 | Fink ........................ | 514/19 |
| 5,654,301 A | | 8/1997 | Kohn et al. ............. | 514/231.2 |
| 5,773,475 A | | 6/1998 | Kohn ........................ | 514/616 |
| 5,780,589 A | * | 7/1998 | Lazarus et al. ............ | 530/331 |
| 5,885,999 A | | 3/1999 | Elliot et al. ............ | 514/266.22 |
| 6,037,324 A | * | 3/2000 | Schwender et al. ......... | 514/18 |
| 6,126,939 A | * | 10/2000 | Eisenbach-Schwartz et al. ................ | 424/185.1 |
| 6,133,261 A | | 10/2000 | Harris .................... | 514/231.2 |
| 6,180,611 B1 | * | 1/2001 | Montana et al. ............ | 514/19 |
| 6,228,875 B1 | | 5/2001 | Tsai et al. ................ | 514/380 |
| 6,737,408 B1 | * | 5/2004 | Balasubramanium et al. . | 514/18 |

FOREIGN PATENT DOCUMENTS

| | | |
|---|---|---|
| EP | 0 997147 A1 | 7/1998 |
| EP | 1 084 704 A1 | 3/2001 |
| WO | WO 99/03460 | 1/1999 |
| WO | WO 99/43309 | 9/1999 |
| ZA | 98/5940 | 7/1998 |

OTHER PUBLICATIONS

Raffa Robert B, Rheumatic diseases clinics of North America, (Nov 2003) 29 (4) 733–45.*
Schaible Hans–Georg, Annals of the New York Academy of Sciences, (Jun 2002) 966 343–54.*
Lowry, Thomas (Mechanism and Theory in Organic Chemistry, pp. 60–71, Harper & Row, New York, 1976).*
Ritchie, Prog Phys Org Chem, vol 2, 323, 1964.*
Konttinen Y. T. (Arthritis and rheumatism 37 (7) 965–82, 1994).*

Kidd B. L., British Journal of Anaesthesia, (Jul 2001) 87 (1) 3–11.*
Shimohigashi, J Biol. Chem. 271, 23642, 1996.*
Kohn H. et al., "Synthesis and anticonvulsant activities of α–heterocyclic α–acetamido–N–benzylacetamide derivatives", Journal of Medicinal Chemistry, United States Oct. 29, 1993, vol. 36, No. 22, pp. 3350–3360, ISSN: 0022–2623, p. 3355, col. 1, paragraph 2, example 3F; table 1.
Shridhar V. Andurkar, et al., "The Anticonvulsant Activities of N–Benzyl 3–Methoxypropionamides", Bioorganic & Medicinal Chemistry 7 (1999), pp. 2381–2389, p. 2381, col. 2; example 3, p. 2385, col. 1, paragraph 2–paragraph 3, XP001097157.
Claudio Toniolo, et al., "A crystal–state, solution and theoretical study of the preferred conformation of linear C. $^{\alpha,\alpha}$–diphenylglycine derivatives and dipeptides with potential anticonvulsant activity", Int. J. Pept. Protein Res. 44. 1994, 85–95, XP001074241, , p. 85, col. 1, paragraph 2, p. 86, col. 1; example XIV.
Claudio Toniolo, et al., "A crystal–state, solution and theoretical study of the preferred conformation of linear C. $^{\alpha,\alpha}$–diphenylglycine derivatives and dipeptides with potential anticonvulsant activity", Int. J. Pept. Protein Res. 44. 1994, 85–95, XP001074241,, p. 85, col. 1, paragraph 2, p. 86, col. 1; example XIV.
Solomon H. Snyder, et al., D–Amino Acids as Putative Neurotransmitters: Focus on D–Serine, Neurochemical Research, vol. 25, No. 5, 2000, pp. 553–560.
Abstract of International Application No. WO 99/02146 dated Jan. 21, 1999.
David E. Baranan et al., "Atypical neural messengers", TRENDS in Neurosciences, vol. 24, No. 2, Feb. 2001, pp. 99–106.
J.M. Elliott, et al., "Serine Derived NK, Antagonists 1: The Effect of Modifications to the Serine Substituents", Bioorganic & Medical Chimistry Letters 8 (1998) pp. 1845–1850.
Solomon H. Snyder, M.D., et al., "Novel Neurotransmitters and their Neuropsychiatric Relevance", Am J Psychiatry, 157:11, Nov. 2000, pp. 1738–1751.
Robert Berkow, M.D., et al., "The Merck Manual of Diagnosis and Therapy", Merck Research Laboratories, (1992), pp. 1406–1615.

(Continued)

Primary Examiner—Jon Weber
Assistant Examiner—David Lukton
(74) Attorney, Agent, or Firm—Scully, Scott, Murphy & Presser

(57) ABSTRACT

The present invention is directed to the use of compounds of the formula:

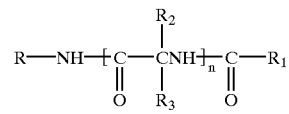

for treating pain, in particular neuropathic pain, bipolar disease and migraine headaches.

54 Claims, No Drawings

OTHER PUBLICATIONS

Harris FRC, and Schwarz Pharma AG, *Windover Information Inc.*, 2000, p. 122.

Herman Wolosker, et al., "Serine racemase: A glial enzyme synthesizing D–serine to regulate glutamate–N–methyl–D–asparatate neurotransmission", *PNAS,* vol. 96, No. 23, Nov. 9, 1999, pp. 13409–13414.

Daeock Choi, "Synthesis, Chemistry, and Biological Evaluation of Medicinally Relevant Compounds", *A Bell & Howell Company,* Dec.,1995, pp. 1–208.

Fu Y, et al., "Systemic nicotine stimulates dopamine release in nucleus accumbens: Re–evaluation of the role of N–methyl–D–aspartate receptors in the ventral tegmental area", *J Pharmacol Exp Ther* 2000,294(2):458–65.

Kohn H. et al., "Synthesis and anticonvulsant activities of α–heterocyclic α–acetamido–N–benzylacetamide derivatives", *Journal of Medicinal Chemistry, United States* Oct. 29, 1993, vol. 36, No. 22, pp. 3350–3360.

Andurkar, et al., "The Anticonvulsant Activities of N–Benzyl 3–Methoxypropionamides", Bioorganic & Medicinal Chemistry 7 (1999), pp. 2381–2389.

Toniolo, et al., "A crystal–state, solution and theoretical study of the preferred conformation of linear C. $^{\alpha,\alpha}$–diphenylglycine derivatives and dipeptides with potential anticonvulsant activity", *Int. J. Pept. Protein Res. 44.* 1994, 85–95, XP001074241, , p. 85, col. 1, paragraph 2, p. 86, col. 1; example XIV.

Billich, et al., "HIV proteinase inhibitors containing 2–aminobenzylstatine as a novel scissile bond replacement: biochemical. and pharmacological characterization", *Antiviral Research 25* (1994) pp. 215–233.

Parsons, et al., "Modulation of NMDA receptors by glycine—introduction to some basic aspects and recent developments", *Amino Acids,* 14: 207–216 (1998).

Wlaz, et al., "Anticonvulsant effects of eliprodil alone or combined with the glycine$_B$ receptor antagonist L–701,324 or the competitive NMDA antagonist CGP 40116 in the amygdala kindling model in rats", *Neuropharmacology,* 38: 243–251 (1999).

Ebert, et al., "Anticonvulsant effects by combined treatment with a glycine$_B$ receptor antagonist and a polyamine site antagonist in amygdala–kindled rats", *European Journal of Pharmacology,* 322: 179–184 (1997).

* cited by examiner

USES FOR AMINO ACID ANTICONVULSANTS

RELATED APPLICATION

The present application is claiming benefit of U.S. Ser. No. 60/228,230 filed on Aug. 25, 2000.

FIELD OF THE INVENTION

The present invention is directed to the novel uses of a peptide class of compounds for treating bipolar disorders and headaches, such as migraines and pain, especially neuropathic pain.

BACKGROUND OF THE INVENTION

Bipolar disorders and headaches, such as migraines, and pain, including neuropathic pain, are varied maladies that on its face, are diverse.

A migraine headache is defined as a periodically occurring vascular headache characterized by pain in the head (usually unilateral), nausea, and vomiting, photophobia, phenophobia, vertigo and general weakness. Migraine is the most common type of vascular headache and affects as many as 15% of the world's population. Of the different types of migraines, classical migraine and common migraine are the two most prevalent. The major difference between the two types of migraines is that classical migraines are preceded by the appearance of neurological symptoms before an attack whereas common migraines are not preceded by such symptoms. Migraine is caused by intermittent brain dysfunction. However, the precise pathophysiological mechanisms involved are not understood. The head-pain is believed to involve blood vessel dilation and a reduction in the brain's pain relieving chemicals.

Neuropathic pain, on the other hand, can be described as pain associated with damage or permanent alteration of the central nervous system. Clinical manifestations of neuropathic pain include a sensation of burning or electric shock, feelings of bodily distortion, allodynia and hyperalgesia.

It results from injury to a nerve. In contrast to the immediate pain caused by tissue injury, neuropathic pain can develop days or months after a traumatic injury. Furthermore, while pain caused by tissue injury is usually limited in duration to the period of tissue repair, neuropathic pain frequently is long lasting or chronic.

Moreover, neuropathic pain can occur spontaneously or as a result of stimulation that normally is not painful.

The clinical causes of neuropathic pain are widespread and include both trauma and disease. For example, traumatic nerve compression, or crush, and traumatic injury to the brain or spinal cord are common causes of neuropathic pain. Furthermore, most traumatic nerve injuries also cause the formation of neuromas, in which pain occurs as a result of aberrant nerve regeneration. In addition, cancer-related neuropathic pain is caused when tumor growth painfully compresses adjacent nerves, the brain or the spinal cord. Neuropathic pain is associated with diseases such as diabetes or alcoholism.

Bipolar disorder is a neuropsychiatric disorder. Also known as bipolar affective disorder (BAD) or manic-depressive illness, it is characterized by episodes of elevated mood (mania) and depression. The most severe and clinically distinctive forms of BAD are BP-I (severe bipolar affective (mood) disorder), which affects 2–3 million people in the U.S. and SAD-M (schizoaffective disorder manic type). They are characterized by at least one full episode of mania, with or without episodes of major depression (defined by lower mood or depression, with associated disturbances in rhythmic behaviors, such as sleeping, eating and sexual activity).

The therapies are varied. Analgesics are often used to treat infrequent and mild migraines. Analgesics reduce the pain of a migraine and in the case of aspirin also discourage clumping of blood platelets. However, for moderate to severe migraines, stronger medication is necessary, e.g., ergotamine or 5-H-$T_1$ agonists, like sumatriptan.

On the other hand, for neuropathic pain, opioid compounds (opiates) such as morphine may be utilized to treat the malady. Although effective as an analgesic, it is not always effective in treating neuropathic pain and may induce tolerance in patients. When a subject is tolerant to opioid narcotics, increased doses are required to achieve a satisfactory analgesic effect. At high doses, these compounds produce side effects, such as respiratory depression, which can be life threatening. In addition, opioids frequently produce physical dependence in patients, which may be related to the dose of opioid taken and the period of time over which it is taken by the subject.

But neuropathic pain and bipolar disorder frequently are resistant to available drug therapies. In addition, current therapies have serious side-effects including, for example, cognitive changes, sedation, nausea, and in the case of narcotic drugs addictions. Many patients suffering from neuropathic pain are elderly or have other medical conditions that particularly limit their tolerance of the side-effects associated with available drug therapy.

The inadequacy of current therapy in relieving neuropathic pain and bipolar disorders without producing intolerable side-effects frequently is manifested in the depression and suicidal tendency of chronic pain sufferers. Moreover, the present drugs are not effective for completely alleviating the pain from those who have moderate to heavy migraine headaches.

U.S. Pat. No. 5,885,999 discloses compounds which are useful for treating various maladies such as pain and headaches including migraines. These compounds are serine derivatives of the formula:

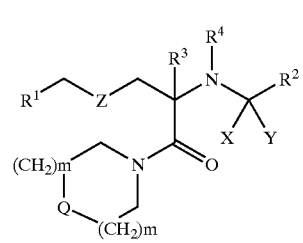

(1)

wherein m is zero, 1 or 2; and n is zero or 1, with the proviso that the sum total of m+n is 1 or 2;

$R^1$ represents phenyl; naphthyl; benzohydryl; or benzyl, where the naphthyl group or any phenyl moiety may be substituted;

$R^2$ represents hydrogen; phenyl; heteroaryl selected from indazolyl, thienyl, furanyl, pyridyl, thiazolyl, tetrazolyl and quinolinyl; naphthyl; benzohydryl; or benzyl; wherein each heteroaryl, napthyl group and any phenyl moiety may be substituted;

$R^3$ and $R^4$ each independently represents hydrogen or $C_{1-6}$alkyl or $R^3$ and $R^4$ together are linked so as to form a $C_{1-3}$alkylene chain;

Q represents CR$^5$R$^6$ or NR$^5$;

X and Y each independently represents hydrogen, or together form a group=O; and

Z represents a bond O, S, SO, SO$_2$, NR$^c$ or —(CR$^c$R$^d$)-m where R$^c$ and R$^d$ each independently represent hydrogen or C$_{1-6}$alkyl;

or a pharmaceutically acceptable salt thereof.

The compounds are alleged to be also useful in the treatment or prevention of inflammation, emesis and postherapeutic neuralgia.

In U.S. Pat. No. 6,228,825 to Tsai, et al., other amino acids and derivatives thereof are alleged to be useful for treating neuropsychiatric disorders, such as schizophrenia, Alzheimer's Disease, depression, autism, closed head injury, benign forgetfulness, childhood learning disorders, and attention deficit disorders. These drugs include (i) D-alanine or modified form thereof, provided that the composition is substantially free of D-cycloserine and/or (ii) serine (or a modified from thereof), and/or (iii) 105 to 500 mg of D-cycloserine (or a modified form thereof); and/or (iv) N-methylglycine (or a modified form thereof).

D-cycloserine, D-serine esters, D-serine or salts thereof have been disclosed to be useful in treating spinocerebellar degeneration. See, EP Application No. 1,084,704.

Peptides have also been alleged to be useful for treatment of pain and neurosis. More specifically, EPO application 997,147 discloses compounds of the formula:

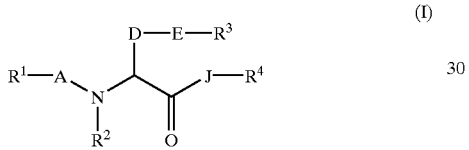

(I)

wherein

R$^1$ is
1) C1–15 alkyl,
2) C1–8 alkoxy,
3) phenyl,
4) C3–8 cycloalkyl,
5) hetero ring,
6) C1–4 alkyl substituted by phenyl, C3–8 cycloalkyl, or hetero ring,
7) C1–4 alkoxy substituted by phenyl, C3–8 cycloalkyl, or hetero ring, or
8) C2–4 alkenyl substituted by phenyl, C3–8 cycloalkyl, or hetero ring (with proviso that, all phenyl, C3–8 cycloalkyl and hetero ring in R$^1$ group may be substituted by 1–3 substituent selected from the following (i)–(xi):
 (i) C1–4 alkyl,
 (ii) C1–4 alkoxy,
 (iii) phenyl,
 (iv) phenoxy,
 (v) benzyloxy,
 (vi) —SR$^5$ (in which R$^5$ is hydrogen or C1–4 alkyl),
 (vii) C2–5 acyl,
 (viii) halogen,
 (ix) C1–4 alkoxycarbonyl,
 (x) nitro,
 (xi) —NR$^6$R$^7$ (in which R$^6$ and R$^7$ each independently, is hydrogen, C1–4 alkyl or C1–4 alkoxycarbonyl, or R$^6$ and R$^7$ taken together with the nitrogen atom to which they are attached may represent 5–7 membered saturated hetero ring containing another one nitrogen atom or one oxygen atom));

A is a bond, —CO— or —SO$^2$—;

R$^2$ is hydrogen or C1–4 alkyl optionally substituted by one phenyl;

D is C1–4 alkylene or C2–4 alkenylene;

E is
1) —COO—,
2) —OCO—,
3) —CONR$^8$ (in which R$^8$ is hydrogen or C1–4 alkyl),
4) —NR$^9$CO— (in which R$^9$ is hydrogen or C1–4 alkyl),
5) —O—,
6) —S—,
7) —SO—,
8) —SO$_2$—,
9) —NR$^{10}$— (in which R$^{10}$ is hydrogen or C1–4 alkyl),
10) —CO—,
11) —SO$_2$NR$^{11}$— (in which R$^{11}$ is hydrogen or C1–4 alkyl) or
12) —NR$^{12}$SO$_2$— (in which R$^{12}$ is hydrogen or C1–4 alkyl);

R$^3$ is
1) carbocyclic ring,
2) hetero ring, or
3) C1–4 alkyl substituted by carbocyclic ring or hetero ring (with proviso that, all carbocyclic ring and hetero ring in R$^3$ may be substituted by 1–3 substituents selected from the following (i)–(xi);
 (i) C1–4 alkyl,
 (ii) C1–4 alkoxy,
 (iii) phenyl,
 (iv) phenoxy,
 (v) benzyloxy,
 (vi) —SR$^{13}$ (in which R$^{13}$ is hydrogen or C1–4 alkyl),
 (vii) C2–5 acyl,
 (viii) halogen,
 (ix) C1–4 alkoxycarbonyl,
 (x) nitro,
 (xi) —NR$^{14}$R$^{15}$ (in which R$^{14}$ and R$^{15}$, each independently, is hydrogen, C1–4 alkyl or C1–4 alkoxycarbonyl, or R$^{14}$ and R$^{15}$ taken together with the nitrogen atom to which they are attached may represent 5–7 membered saturated hetero ring containing another one nitrogen atom or one oxygen atom);

J is —O— or —NR$^{16}$— (in which R$^{16}$ is hydrogen or C1–4 alkyl);

R$^4$ is
1) C1–8 alkyl,
2) carbocyclic ring,
3) hetero ring,
4) C1–8 alkyl substituted by 1–3 of substituent selected from the following (i)–(v);
 (i) carbocyclic ring,
 (ii) hetero ring,
 (iii) COOR$^{17}$ (in which R$^{17}$ is hydrogen or C1–4 alkyl substituted by one phenyl (in which phenyl may be substituted by C1–4 alkoxy),
 (iv) SR$^{18}$ (in which R$^{18}$ is hydrogen or C1–4 alkyl),
 (v) OR$^{19}$ (in which R$^{19}$ is hydrogen or C14 alkyl), or when J represents —NR$^{16}$— group, R$^4$ and R$^{16}$ taken together with the nitrogen atom to which they are attached may represent hetero ring (with proviso that, all carbocyclic ring and hetero ring, and hetero ring represented by R$^4$ and R$^{16}$ taken together with the nitrogen atom to which they are attached may be substituted by 1–3 of substituent selected from the following (i)–(xi);
(i) C1–4 alkyl,
(ii) C1–4 alkoxy,
(iii) phenyl,
(iv) phenoxy,
(v) benzyloxy,
(vi) —SR$^{20}$ (in which R$^{20}$ is hydrogen or C1–4 alkyl),
(vii) C2–5 acyl,
(viii) halogen,
(ix) C1–4 alkoxycarbonyl,
(x) nitro,
(xi) —NR$^{21}$R$^{22}$ (in which R$^{21}$ and R$^{22}$ each independently, is hydrogen, C1–4 alkyl or C1–4 alkoxycarbonyl, or R$^{21}$ and R$^{22}$ taken together with the nitrogen atom to which they are attached may represent 5–7 membered saturated hetero ring containing another one nitrogen atom or one oxygen atom), non-toxic salt thereof, or a hydrate thereof.

Other peptides are known to exhibit central nervous system (CNS) activity and are useful in the treatment of epilepsy and other CNS disorders. These peptides, which are described in U.S. Pat. No. 5,378,729, to Kohn, et al., have the formula:

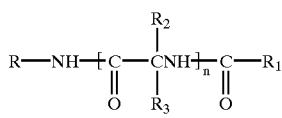

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

R$_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and R$_2$ and R$_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein R$_2$ and R$_3$ may be unsubstituted or substituted with at least one electron withdrawing group or electron donating group;

Z is O, S, S(O)$_a$, NR$_4$, PR$_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo; Z is a chemical bond, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$ or PR$_4$SR$_7$, NR$_4$PR$_5$R$_6$ or PR$_4$NR$_5$R$_7$,

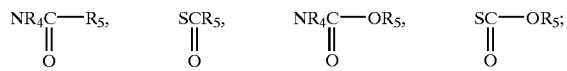

R$_4$, R$_5$ and R$_6$ are independently hydrogen, lower alkyl, aryl, aryl lower alkyl, lower alkenyl, or lower alkynyl, wherein R$_4$, R$_5$ and R$_6$ may be unsubstituted or substituted with an electron withdrawing group or an electron donating group; and R$_7$ is R$_6$ or COOR$_8$ or COR$_8$;

R$_8$ is hydrogen or lower alkyl, or aryl lower alkyl, and the aryl or alkyl group may be unsubstituted or substituted with an electron withdrawing group or an electron donating group; and n is 1–4; and a is 1–3.

U.S. Pat. No. 5,773,475, the contents of which are incorporated by reference, also discloses additional compounds useful for treating CNS disorders. These compounds are N-benzyl-2-amino-3-methoxy-propionamides having the formula:

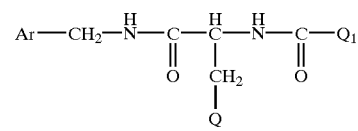

wherein

Ar is aryl which is unsubstituted or substituted with halo;

Q is lower alkoxy; and

Q$_1$ is CH$_3$.

Harris in U.S. Pat. No. 6,133,261 describes a method of treating or preventing stroke in a human by administering thereto an effective amount of a compound of the formula:

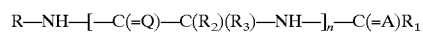

wherein

R is hydrogen, lower alkyl, lower alkenyl, lower alkynyl, aryl, aryl (lower alkyl), heterocyclic, heterocyclic (lower alkyl), (lower alkyl) heterocyclic, lower cycloalkyl, lower cycloalkyl (lower alkyl), and R is unsubstituted or is substituted with at least one electron withdrawing group, or electron donating group;

R$_1$ is hydrogen or lower alkyl, lower alkenyl, lower alkynyl, aryl (lower alkyl), aryl, heterocyclic, (lower alkyl) heterocyclic, heterocyclic (lower alkyl), lower cycloalkyl, lower cycloalkyl (lower alkyl), each unsubstituted or substituted with an electron donating group or an electron withdrawing group and R$_2$ and R$_3$ are independently hydrogen, lower alkyl, lower alkenyl, lower alkynyl, aryl (lower alkyl), aryl, heterocyclic, heterocyclic (lower alkyl), (lower alkyl) heterocyclic, lower cycloalkyl, lower cycloalkyl (lower alkyl), SO$_3^-$, or Z-Y where R$_2$ and R$_3$ may be unsubstituted or substituted with at least one electron withdrawing group or electron donating group;

Z is O, S, S(O)$_a$, NR$_4$, PR$_4$ or a chemical bond;

Y is hydrogen, lower alkyl, aryl, aryl(lower alkyl), lower alkenyl, lower alkynyl, halo, heterocyclic, heterocyclic (lower alkyl), (lower alkyl)heterocyclic, cycloalkyl, cycloalkyl (lower alkyl) and Y may be unsubstituted or substituted with an electron donating group or an electron withdrawing group, provided that when Y is halo, Z is a chemical bond;

or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$, PR$_4$SR$_7$, NR$_4$PR$_5$R$_6$, PR$_4$NR$_5$R$_7$, NR$_4$C(O)R$_5$, SC(O)R$_5$, NR$_4$CO$_2$R$_5$, SCO$_2$R$_5$, NR$_4$C(O)R$_5$R$_6$, NR$_4$C(O)NR$_5$S(O)$_a$R$_6$, NR$_4$C(S)R$_5$R$_6$, NR$_4$C(=Q)MNR$_5$C(=A)OR$_6$, or C(S)NH$_2$;

R$_4$, R$_5$ and R$_6$ are independently hydrogen, lower alkyl, aryl, aryl (lower alkyl), lower alkenyl, or lower alkynyl, wherein R$_4$, R$_5$ and R$_6$ may be unsubstituted or substituted with an electron withdrawing group or an electron donating group;

R$_7$ is R$_6$, COOR$_8$, or C(O)R$_8$;

R$_8$ is hydrogen or lower alkyl, or aryl (lower alkyl), and the aryl or alkyl group may be unsubstituted or substituted with an electron withdrawing group or an electron donating group;

A and Q are independently O or S;

M is an alkylene chain containing up to 6 carbon atoms or a chemical bond;

n is 1–4; and a is 1–3;

or a pharmaceutically acceptable salt thereof.

The present inventor has found that these peptides in U.S. Pat. Nos. 5,378,729 and 5,773,475, are useful for treating pain, including neuropathic pain, and headaches, including migraines and bipolar disorders. Moreover, these compounds are not addictive and do not exhibit the side effects of the commercially available drugs described hereinabove.

SUMMARY OF THE INVENTION

Accordingly, the present invention is directed to the method of treating bipolar disease in a patient suffering from same which comprises administering thereto an amount effective to treat such bipolar disease of a compound having Formula I:

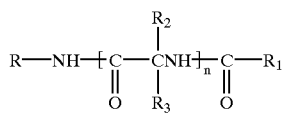

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group, or electron donating group;

R$_1$ is hydrogen or lower alkyl, lower alkenyl, lower alkynyl, aryl lower alkyl, aryl, heterocyclic lower alkyl, heterocyclic, lower alkyl heterocyclic, lower cycloalkyl, lower cycloalkyl lower alkyl, each unsubstituted or substituted with an electron donating group or an electron withdrawing group; and R$_2$ and R$_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, halo or Z-Y wherein R$_2$ and R$_3$ may be unsubstituted or substituted with at least one electron withdrawing group or electron donating group;

Z is O, S, S(O)$_a$, NR$_4$, or PR$_4$;

Y is hydrogen, lower alkyl, aryl, aryl lower alkyl, lower alkenyl, lower alkynyl, halo, heterocyclic, heterocyclic lower alkyl, lower alkyl heterocyclic, lower cycloalkyl, lower cycloalkyl lower alkyl, and Y may be unsubstituted or substituted with an electron donating group or an electron withdrawing group, or ZY taken together is NR$_4$NR$_5$R$_7$, NR$_4$OR$_5$, ONR$_4$R$_7$, OPR$_4$R$_5$, PR$_4$OR$_5$, SNR$_4$R$_7$, NR$_4$SR$_7$, SPR$_4$R$_5$ or PR$_4$SR$_7$, NR$_4$PR$_5$R$_6$ or PR$_4$NR$_5$R$_7$,

R$_4$, R$_5$ and R$_6$ are independently hydrogen, lower alkyl, aryl, aryl lower alkyl, lower alkenyl, or lower alkynyl, wherein R$_4$, R$_5$ and R$_6$ may be unsubstituted or substituted with an electron withdrawing group or an electron donating group;

R$_7$ is independently R$_6$ or COOR$_8$ or COR$_8$;

R$_8$ is hydrogen or lower alkyl, or aryl lower alkyl, and the aryl or alkyl group may be unsubstituted or substituted with an electron withdrawing group or an electron donating group; and n is 1–4; and a is 1–3.

The present invention is also directed to the method of treating pain in a patient suffering from same which comprises administering to said patient a pain alleviating effective amount of said compound to treat the pain.

In another aspect, the present invention is directed to a method of treating headaches, including migraine headaches, in a patient suffering from same which comprises administering to said patient a headache alleviating effective amount of said compound.

DETAILED DESCRIPTION OF THE INVENTION

As indicated hereinabove, the compounds of Formula I are useful for treating pain, including neuropathic pain and headaches, including migraine headaches, and bipoloar disorders. These compounds are described in U.S. Pat. No. 5,378,729, the contents of which are incorporated by reference.

As defined herein, the "alkyl" groups when used alone or in combination with other groups, are lower alkyl containing from 1 to 6 carbon atoms and may be straight chain or branched. These groups include methyl, ethyl, propyl, isopropyl, butyl, isobutyl, tertiary butyl, amyl, hexyl, and the like.

The "aryl lower alkyl" groups include, for example, benzyl, phenethyl, phenpropyl, phenisopropyl, phenbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. A polynuclear aromatic compound, as used herein, is meant to encompass bicyclic and tricyclic fused aromatic ring systems containing from 10–18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocyenyl.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1,3- or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16–18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy; mercapto, lower alkylthio, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl.

As employed herein, the heterocyclic substituent contains at least one sulfur, nitrogen or oxygen ring atom, but also may include one or several of said atoms in the ring, but preferably no more than 4 heteroatoms in the ring. The heterocyclic substituents contemplated by the present invention include heteroaromatics and saturated and partially saturated heterocyclic compounds. These heterocyclics may be monocyclic, bicyclic, tricyclic or polycyclic and are fused rings. They may contain from 3 up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the nitric oxides of pyridyl, pyrazinyl, and pyrimidinyl and the like. The preferred heterocyclics are thienyl, furyl, pyrrolyl, benzofuryl, benzothienyl, indolyl, methylpyrrolyl, morpholinyl, pyridyl, pyrazinyl, imidazolyl, pyrimidinyl, and pyridazinyl. The preferred heterocyclic is a 5 or 6-membered heterocyclic compound. The especially preferred heterocyclic is furyl, pyridyl, pyrazinyl, imidazolyl, pyrimidinyl, and pyridazinyl. The most preferred heterocyclic is furyl, pyridyl, thiazolyl and thienyl.

The preferred compounds are those wherein n is 1, but di, tri and tetrapeptides are also contemplated to be within the scope of the claims.

The preferred values of R is aryl lower alkyl, especially benzyl, especially those wherein the phenyl ring thereof is unsubstituted or substituted with electron donating groups or electron withdrawing groups, such as halo (e.g., F).

The preferred $R_1$ is H or lower alkyl. The most preferred $R_1$ group is methyl.

The most preferred electron donating substituents and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amino lower alkyl, mercapto, lower alkylthio, and lower alkyldithio. The term "sulfide" encompasses mercapto, and alkylthio, while the term disulfide encompasses alkyldithio. It is more preferred that the electron donating groups and electron withdrawing groups do not contain a cyclic group. The electron donating and electron withdrawing groups may be substituted on any one of $R_1$, $R_2$, $R_3$, $R_4$, $R_5$ or $R_6$, $R_7$ or $R_8$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt; hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein R$_{18}$ is lower alkyl], N-lower alkylhydroxyl amino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl] and o-hydroxylamino (—O—NH$_2$); alkylamido such as acetamido; trifluoroacetamido; lower alkoxyamino, (e.g., NH(OCH$_3$); and heterocyclicamino, such as pyrazoylamino.

The preferred heterocyclic groups representative of $R_2$ and $R_3$ are monocyclic heterocyclic moieties of the formula:

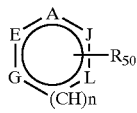

XI or those corresponding partially or fully saturated form thereof wherein n is 0 or 1; and $R_{50}$ is H or an electron withdrawing group or electron donating group;

A, Z, L and J are independently CH, or a heteroatom selected from the group consisting of N, O, S; and G is CH, or a heteroatom selected from the group consisting of N, O and S, but when n is O, G is CH, or a heteroatom selected from the group consisting of NH, O and S with the proviso that at most two of A, E, L, J and G are heteroatoms.

When n is O, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

Thus, the most preferred monocyclic heterocyclic definition of $R_2$ and $R_3$ is furyl thienyl, thiazolyl, and pyridyl.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is O, $R_2$ or $R_3$ may additionally be bonded to the main chain by a nitrogen ring atom.

Other preferred moieties of $R_2$ and $R_3$ are hydrogen, aryl, e.g., phenyl, aryl alkyl, e.g., benzyl and alkyl.

It is to be understood that the preferred groups of $R_2$ and $R_3$ may be unsubstituted or substituted with electron donating or electron withdrawing groups. It is preferred that the electron withdrawing group or electron donating group does not contain a cyclic group, unless the electron withdrawing group or electron donating group is a hydrocarbyl group that contains only carbon and hydrogen atoms.

It is more preferred that $R_2$ and $R_3$ are independently hydrogen, lower alkyl, which is either unsubstituted or substituted with an electron withdrawing group or an electron donating group, such as lower alkoxy (e.g., methoxy, ethoxy, and the like), N-hydroxylamino, N-lower alkylhydroxyamino, N-loweralkyl-O-loweralkyl and alkylhydroxyamino.

It is even more preferred that one of $R_2$ and $R_3$ is hydrogen; while the other is one of the preferred group indicated hereinabove.

It is preferred that n is one.

It is preferred that $R_2$ is hydrogen and $R_3$ is hydrogen, an alkyl group which is unsubstituted or substituted by at least an electron donating or electron withdrawing group or ZY. In this preferred embodiment, it is more preferred that $R_3$ is hydrogen or an alkyl group such as methyl, which is unsubstituted or substituted by an electron donating group, $NR_4OR_5$ or $ONR_4R_7$, wherein $R_4$, $R_5$ and $R_7$ are independently hydrogen or lower alkyl. It is preferred that the electron donating group is lower alkoxy, and especially methoxy or ethoxy.

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred $R_1$ is loweralkyl, especially methyl.

The more preferred compounds are compounds of formula I wherein n is 1; $R_2$ is hydrogen; $R_3$ is hydrogen, an alkyl group, especially methyl which is substituted by an electron donating or electron withdrawing group or ZY; R is aryl, aryl lower alkyl, such as benzyl, wherein the aryl group is unsubstituted or substituted and $R_1$ is lower alkyl. In this embodiment, it is most preferred that $R_3$ is hydrogen, an alkyl group, especially methyl, substituted by electron donating group, such as lower alkoxy, (e.g., methoxy, ethoxy and the like), $NR_4OR_5$ or $ONR_4R_7$ wherein these groups are defined hereinabove.

The most preferred compounds utilized are those of the formula:

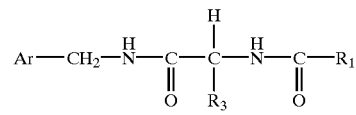

wherein

Ar is aryl, especially phenyl, which is unsubstituted or substituted with at least one electron donating group or electron withdrawing group;

$R_1$ is lower alkyl; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, such as alkoxy, or $NR_4OR_5$ or $ONR_4R_7$. It is most preferred that $R_3$ is $CH_2$—Q, wherein Q is lower alkoxy, $NR_4OR_5$ or $ONR_4R_7$ wherein $R_4$ is hydrogen or alkyl containing 1–3 carbon atoms, $R_5$ is hydrogen or alkyl containing 1–3 carbon atoms, and $R_7$ is hydrogen or alkyl containing 1–3 carbon atoms.

The preferred $R_1$ is $CH_3$.

The most preferred aryl is phenyl.

The most preferred compounds include:

(R)-N-Benzyl-2-acetamido-3-methoxy-propionamide

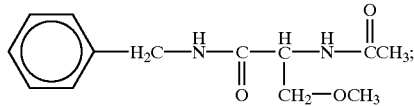

O-methyl-N-acetyl-D-serine-m-fluorobenzyl-amide

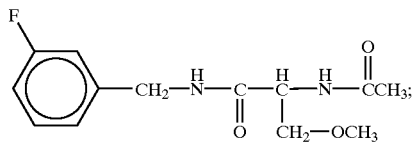

O-methyl-N-acetyl-D-serine-p-fluorobenzylamide

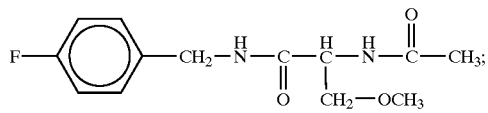

N-acetyl-D-phenylglycinebenzylamide

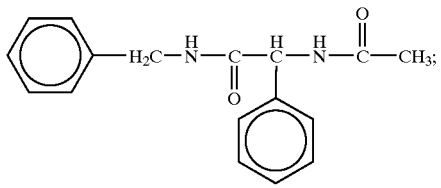

D-1,2-(N, O-dimethylhydroxylamino)-2-acetamide acetic acid benzylamide

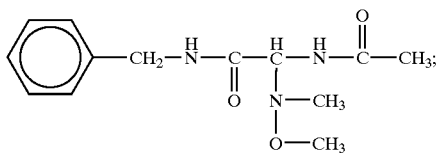

D-1,2-(O-methylhydroxylamino)-2-acetamido acetic acid benzylamide

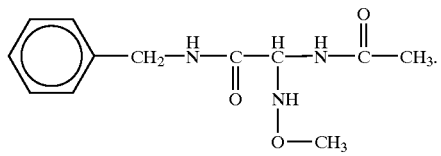

Some of the preferred compounds are described in U.S. Pat. No. 5,773,475, the contents of which are incorporated by reference.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the various Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one (1) or more asymmetric carbons and may exist in racemic and optically active forms. The configuration around each asymmetric carbon can be either the D or L form. (It is well known in the art that the configuration around chiral carbon atoms can also be described as R or S in the Cahn-Prelog-Ingold nomenclature system). All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention are of the formula

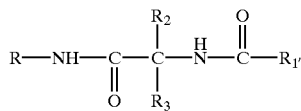

wherein R, $R_1$, $R_2$, $R_3$, $R_4$, $R_5$, $R_6$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

Depending upon the substituents, the present compounds may form addition salts as well. All of these forms are contemplated to be within the scope of this invention, including mixtures of the stereoisomeric forms. The following three schemes of preparation are generally exemplary of the process of which can be employed for the preparation of the compounds utilized. These are described in U.S. Pat. Nos. 5,378,729 and 5,773,475, the contents of both of which are incorporated by reference.

Scheme I

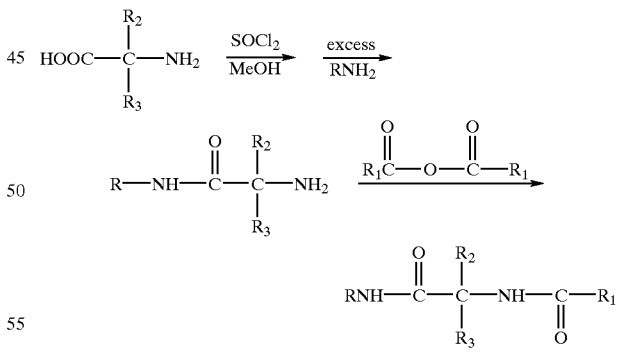

Scheme II

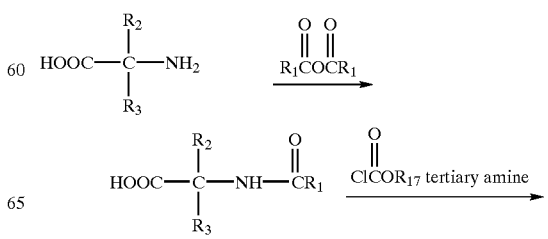

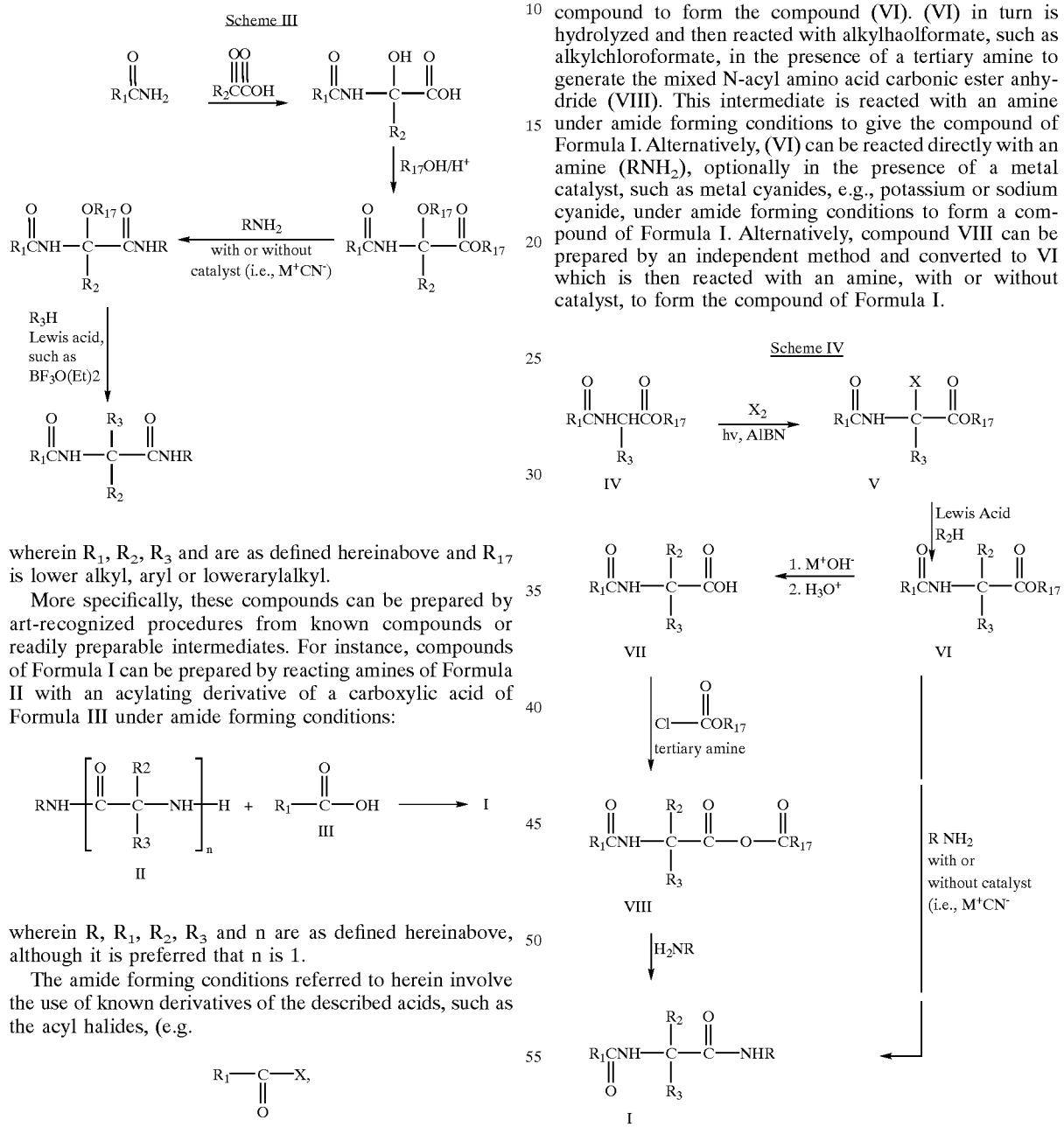

When alkyl esters are employed, amide bond formation can be effected by metal cyanides such as sodium or potassium cyanides.

Another exemplary procedure for preparing compounds wherein at least one of $R_2$ and $R_3$ is aromatic or heteroaromatic is depicted in Scheme IV.

The ester (IV) is reacted with halogen and ultraviolet light in the presence of a catalyst, e.g., AIBN, to form the halo derivative (V). (V) is reacted in the presence of a Lewis acid, such as zinc chloride, with an aromatic or heteroaromatic compound to form the compound (VI). (VI) in turn is hydrolyzed and then reacted with alkylhaolformate, such as alkylchloroformate, in the presence of a tertiary amine to generate the mixed N-acyl amino acid carbonic ester anhydride (VIII). This intermediate is reacted with an amine under amide forming conditions to give the compound of Formula I. Alternatively, (VI) can be reacted directly with an amine ($RNH_2$), optionally in the presence of a metal catalyst, such as metal cyanides, e.g., potassium or sodium cyanide, under amide forming conditions to form a compound of Formula I. Alternatively, compound VIII can be prepared by an independent method and converted to VI which is then reacted with an amine, with or without catalyst, to form the compound of Formula I.

wherein
X=halogen (i.e., Cl, Br);
$R_{17}$=lower alkyl, aryl, or aryl lower alkyl; and
M+=metal cation (i.e., $Na^+$, $K^+$)

Two additional synthetic routes may be employed for the preparation of compounds wherein $R_2$ or $R_3$ is Z-Y as defined hereinabove. In one scheme, for the preparation of these complexes, a substitution reaction is used:

Scheme V

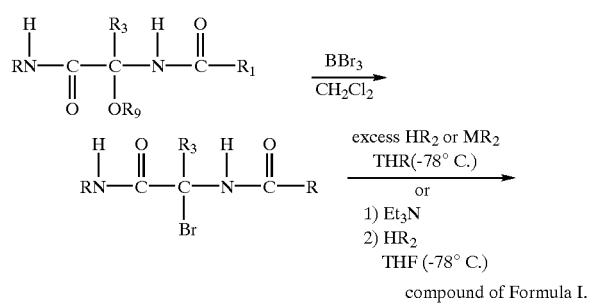

In the above scheme, $R_9$ is lower alkyl, $R_2$ is Z-Y and Z, Y, R, $R_3$ and $R_1$ are as defined hereinabove and M is a metal.

The ether functionality on IX can be cleaved by treatment with Lewis acids, such as $BBr_3$, in an inert solvent such as methylene chloride to form the corresponding halo (bromo) derivative. Addition of either an excess of H—$R_2$ or $MR_2$ or the sequential addition of triethylamine and H—$R_2$ to a THF mixture containing the halo derivative furnishes the desired product. For example, in the case wherein the compound of Formula IX is 2-acetamido-N-benzyl-2-ethoxy acetamide, its treatment with $BBr_2$ in $CH_2Cl_2$ led to the formation of the α-bromo derivative, 2-acetamido-N-benzyl-2-bromoacetamide. Addition of an excess of $HR_2$ or the sequential addition of triethylamine and $HR_2$ to the THF mixture containing the bromo adduct furnishes the desired product.

In another procedure, the product wherein $R_2$ or $R_3$ is Z-Y can also be prepared by a substitution reaction on a quaternary ammonium derivative of the compound of Formula I as outlined below:

Scheme VI

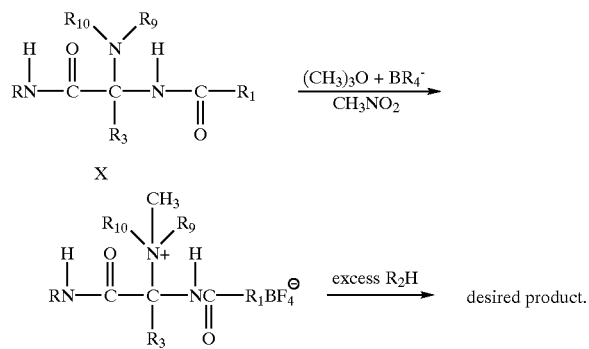

In scheme VI, R, $R_1$, $R_3$ and R are as defined hereinabove, $R_2$ is Z-Y and $R_9$ and $R_{10}$ are independently lower alkyl. In scheme VI, methylation of compound X with a methylation reagent, such as trimethyloxonium tetrafluoroborate, provided the corresponding ammonium derivative. Subsequent treatment of the ammonium salt with $HR_2$ furnishes the desired product. For example, methylation of 2-acetamido-N-benzyl-2-(N,N-dimethylamino)acetamide with trimethyloxonium tetrafluoroborate in nitromethane furnished the quaternary ammonium derivative, 2-acetamido-N-benzyl-(N,N,N-trimethylammonium)acetamide tetrafluoroborate in high yields. Subsequent treatment of the salt with the $HR_2$ reagent in the methanol leads to the production of the desired product.

As in any organic reaction, inert solvents can be employed such as methanol, ethanol, propanol, acetone, tetrahydrofuran, dioxane, dimethylformamide, dichloromethane, chloroform and the like. The reaction is normally effected at or near room temperature, although temperatures from 0° C. up to the reflux temperature of the solvent can be employed.

As a further convenience, the amide forming reaction can be effected in the presence of a base, such as a tertiary organic amine, e.g., triethylamine, pyridine, 4-methylmorpholine, picolines and the like, particularly where hydrogen halide is formed by the amide forming reaction, e.g., the reaction of an acyl halide and the amine of Formula II. Of course, in those reactions where hydrogen halide is produced, any of the commonly used hydrogen halide acceptors can also be used.

The exact mineral acid or Lewis acid employed in the reaction will vary depending on the given transformation, the temperature required for the conversion and the sensitivity of the reagent toward the acid in the reaction mixture.

The various substituents, e.g., as defined in R, $R_1$, $R_2$, and $R_3$, can be present in the starting compounds, added to any one of the intermediates or added after formation of the final products by the known methods of substitution or conversion reactions. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can be then transformed to the corresponding alkyl groups by various methods, including the Woff-Kishner reduction or Clemmenson reduction. Amino groups can be alkylated to form mono, dialkylamino and trialkylamino groups; and mercapto and hydroxy groups can be alkylated to form corresponding thioethers or ethers, respectively. Primary alcohols can be oxidized by oxidizing agents known in the art to form carboxylic acids or aldehydes, and secondary alcohols can be oxidized to form ketones. Thus, substitution or oxidation reactions or a combination thereof can be employed to provide a variety of substituents throughout the molecule of the starting material, intermidiates, or the final product.

In the above reactions, if the substituents themselves are reactive, then the substituents can themselves be protected according to techniques known in the art. A variety of protecting groups known in the art may be employed. Examples of many of these possible groups may be found in "Protective Groups in Organic Synthesis," by T. W. Greene, John Wiley & Sons, 1981.

Resulting mixtures of isomers can be separated into the pure isomers by methods known to one skilled in the art, e.g., by fractional distillation, crystallization and/or chromatography.

The compounds obviously exist in stereoisomeric forms and the products obtained thus can be mixtures of the isomers, which can be resolved. Optically pure functionalized amino acid derivatives can be prepared directly from the corresponding pure chiral intermediate. Racemic products can likewise be resolved into the optical antipodes, for example, by separation of diastereomeric salts thereof, e.g., by fractional crystallization, by selective enzymatic hydrolysis, e.g., papain digestion, or by use of a chiral stationary phase in a chromatographic separation, such as by high pressure liquid chromatography (HPLC). For a discussion of chiral stationary phases for HPLC, See, DeCamp, Chirality, 1, 2–6 (1989), which is incorporated herein by reference with the same force and effect as is fully set forth herein.

For example, a racemic mixture of an intermediate in any of the schemes depicted hereinabove has the formula:

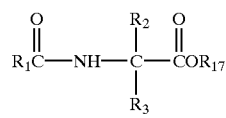

wherein $R_{17}$ is H (which can be prepared according to the procedures of Schemes 1, 2, 3 or 4) is reacted with an optically active amine, $RNH_2$, e.g., (R)(+)α-methylbenzylamine, to form a pair of diastereomeric salts. Diastereomers can then be separated by recognized techniques known in the art, such as fractional recrystallization and the like.

In another method, a racemic mixture of final products or intermediates can be resolved by using enzymatic methods. Since enzymes are chiral molecules, it can be used to separate the racemic modification, since it will preferentially act on one of the compounds, without affecting the enantiomer. For example, acylase, such as acylase I, can be used to separate the racemic modification of an intermediate D, L (±)α-acetamido-2-furanacetic acid. It acts on the L(±)α-acetamido-2-furanacetic acid, but will not act on the D enantiomer. In this way, the D(−)α-acetamido-2-furanacetic acid can be isolated. The intermediate can then react with the amine ($RNH_2$) under amide forming conditions as described hereinabove to form the compound of Formula I.

The compounds utilized in the present invention are useful as such as depicted in the Formula I or can be employed in the form of salts in view of its basic nature by the presence of the free amino group. Thus, the compounds of Formula I form salts with a wide variety of acids, inorganic and organic, including pharmaceutically acceptable acids. The salts with therapeutically acceptable acids are of course useful in the preparation of formulations where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, and the type of malady being treated. He will generally wish to initiate treatment with small dosages substantially less than the optimum dose of the compound and increase the dosage by small increments until the optimum effect under the circumstances is reached. The compounds are useful in the same manner as comparable therapeutic agents and the dosage level is of the same order of magnitude as is generally employed with these other therapeutic agents.

In a preferred embodiment, the compounds utilized are administered in amounts ranging from about 1 mg to about 100 mg per kilogram of body weight per day. This dosage regimen may be adjusted by the physician to provide the optimum therapeutic response. For example, several divided doses may be administered daily or the dose may be proportionally reduced as indicated by the exigencies of the therapeutic situation. The compounds of Formula I may be administered in a convenient manner, such as by oral, intravenous (where water soluble), intramuscular or subcutaneous routes.

The compounds of Formula I may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the active compound of Formula I may be incorporated with excipients and used in the form of ingestible tablets, buccal tablets, troches, capsules, elixirs, suspensions, syrups, wafers, and the like. Such compositions and preparations should contain at least 1% of active compound of Formula I. The percentage of the compositions and preparations may, of course, be varied and may conveniently be between about 5 to about 80% of the weight of the unit. The amount of active compound of Formula I in such therapeutically useful compositions is such that a suitable dosage will be obtained. Preferred compositions or preparations according to the present invention contains between about 10 mg and 6 g of active compound of Formula I.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size, in the case of dispersions, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are the use of vacuum drying and freeze-drying techniques on the active ingredient plus any additional desired ingredients from previously sterile-filtered solution(s) thereof.

As used herein, "pharmaceutically acceptable carrier" includes any and all solvents, dispersion media, coatings, antibacterial and antifungal agents, isotonic and absorption delaying agents for pharmaceutical active substances which are well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage can, for example, contain the principal active compound in amounts ranging from about 10 mg to about 6 g. Expressed in proportions, the active compound is generally present from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, preferably mammals, such as, for example, cats, dogs, horses, cows, pigs, mice, rats and primates, including humans. The preferred patient is human.

The term "treat" refers to either relieving the pain associated with a disease or condition or alleviating the patient's disease or condition.

The compounds of the present invention are useful for treating chronic pain. As used herein, the term "chronic pain" is defined as pain persisting for an extended period of time, for example, greater than three to six months, although the characteristic signs described hereinbelow can occur earlier or later than this period. Vegetative signs, such as lassitude, sleep disturbances, decreased appetite, loss of taste or food, weight loss, diminished libido and constipation develop.

A type of chronic pain that the compounds of the present invention are especially useful in treating is nociceptive pain and neuropathic pain. As used herein, "nociceptive pain" is pain that is judged to be commensurate with on-going activation of pain-sensitive somatic or visceral nerve fibers. This pain is typically experienced as aching or pressure-like when somatic nerves are involved.

On the other hand, neuropathic pain is caused by damage to nerve tissue. The pain may result from nervous system damage involving reorganization of central somato-sensory processing, i.e., differentiation pains (those due to partial or complete interruption of peripheral or central afferent neural activity) and those dependent on sympathetic-mediated pains (those dependent on efferent sympathetic activity). Alternatively, the pain may result from on-going peripheral processes or pathology, such as nerve compression or neuroma formation.

The pain associated with these neuropathic pains is a deep pain, i.e., a spontaneous burning pain often accompanied by a superimposed lancinating component. Other pain sensations, such as hyperesthesia, hyperalgesia, allodynia (pain from a non-noxious stimulant) and hyperpathia (particularly unpleasant, exaggerated pain response) may also be felt by the patient experiencing neuropathic pain.

The compounds of the present invention are administered to a patient suffering from neuropathic pain in an analgesic effective amount. These amounts are equivalent to the therapeutically effective amounts described hereinabove.

Another type of malady experienced by patients for which the compounds of Formula I are useful in treating is headaches, especially migraine headaches.

A migraine headache is a paroxysmal disorder characterized by recurrent attacks of headaches, which may be associated with visual or GI disturbances. In migraine headaches, the pain is usually generalized, but it may also be a unilateral throbbing, which begins around one of the eyes and then spreads through the head to involve one or both sides.

In some severe cases, it is accompanied by anorexia, nausea and vomiting and photophobia. In addition, the extremities are cold and cyanosed, and the patient is irritable. Moreover, the scalp arteries are prominent and their amplitude of pulsation is increased.

The compounds of Formula I are useful in the prophylaxis and the treatment of migraine headaches and alleviating the pain associated therewith. They are administered to patients with migraine headaches in pain relieving effective amounts. These amounts are equivalent to the therapeutically effective amounts described hereinabove. The discussions associated with therapeutic effective amounts are applicable to the treatment and/or prophylaxis of migraine headaches and are incorporated herein.

The compounds of the present invention are also useful in treating patients with bipolar disorders. Bipolar disorders commonly originate with depression and are characterized by at least one elated period during the course of the illness. In bipolar I disorder, major depressive episodes and full-blown manic alternate. In bipolar II disorder, depressive episodes alternate with hypomanias (i.e., mild, non-psychotic periods of excitement) of relatively short duration. These disorders are typically accompanied by the subject experiencing hypersomnia and overeating and these traits may recur on a seasonal basis. Additionally, the patient may suffer from insomnia and poor appetite.

In the full blown bipolar disorder, the mood of the person suffering therefrom is usually elation, but irritability and frank hostility and cantankerousness are also common. The patient is morbid, yet the patient believes that he is in the best mental state. He is psychotic, impatient, intrusive, meddlesome and responds with aggressive irritability when challenged or crossed. The patient may experience interpersonal friction and he may have secondary paranoid delusional interpretations of being persecuted. The patient usually suffers from delusions, especially grand delusions, e.g., false belief of personal wealth, power, inventiveness, genius or importance. The patient may believe that he is being assaulted or persecuted by others. He may even suffer from hallucinations. In the extreme, the psychomotor activity is so frenzied that any understandable link between mood and behavior is lost (delirious mania).

The present compounds are also useful for treating cyclothymic disorders.

The term bipolar disorders, as used herein, also includes mixed states which are rapid alternation between depression and manic manifestations, as for example, momentary switching into tearfulness and suicidal ideas.

The amounts effective for treating bipolar disorders are the therapeutically effective amounts described hereinabove. The discussions associated with therapeutic effective amounts are applicable to the treatment of bipolar disorders and are incorporated herein by reference.

The compounds of the present invention are useful in treating various types of neuroses, especially obsessive-compulsive neurosis.

The former, by definition, is a disorder characterized by the presence of ideas and fantasies which are recurrent, in fact obsessive and by repetitive impulses or actions (compulsions) that the patient recognizes as morbid and toward which he feels a strong inner resistance. The patient himself is anxious, but the anxiety arises in response to internally derived thoughts and disorders that the patient fears he may execute despite a desire to restrain himself.

Again, the amounts described herein are therapeutically effective amounts, which discussions are incorporated herein by reference.

Without wishing to be bound, the compounds of the present invention are believed to interact with the strychnine-insensitive glycine site of the NMDA receptor. By "interact", it is meant that the compounds may be NMDA antagonists, NMDA agonists or partial agonists/antagonists.

The NMDA (N-methyl-D-aspartate) receptor is one of the three major sub-types of glutamate receptors in the CNS. Glutamate, which is believed to be the major excitatory neurotransmitter in the brain, activates the NMDA receptor. The NMDA receptors are found in the membranes of virtually every neuron in the brain. NMDA receptors are ligand gated cation channels that allow $Na^+$, $K^+$, and $Ca^{+2}$ to permeate when they are activated by glutamate, aspartate or NMDA.

However, glutamate alone cannot activate the NMDA receptor. In order to become fully activated by glutamate, the NMDA receptor channel must bind glycine at a specific, high affinity glycine binding site that is separate from the glutamate/NMDA binding site of the receptor protein. Glycine is therefore an obligatory co-agonist at the NMDA receptor/channel complex.

In addition to the binding site for glutamate/NMDA and glycine, the NMDA receptor carries a number of other functionally important binding sites, e.g., $Mg^{2+}$, $Zn^{2+}$, polyamines, arachidonic acid and phencyclidine (PCP).

Without wishing to be bound, it is thus believed that functional modulation of the NMDA subclass of glutamate receptors can be achieved through actions at different recognition sites such as: the primary transmitter site (competitive), the phencyclidine (PCP) site located inside the cation channel (uncompetitive), the polyamine modulatory site, and the strychnine-insensitive glycine site ($glycine_b$).

Without wishing to be bound, it is believed that the compounds of the present invention interact with the glycine binding site of the NMDA receptor. For example, the compounds of the present invention may be antagonists of the glycine binding site of the NMDA receptor.

Glycine is a co-agonist at NMDA receptors and its presence at moderate nM concentrations is a prerequisite for channel activation by glutamate or NMDA. D-serine is also known as an endogenous agonist for the $glycine_b$ receptors. In fact, the D-isomers of serine and alanine are nearly as potent as glycine and considerably more potent than the L-isomers; and these also modulate the $glycine_b$ site. Larger amino acids are less effective. Cycloserine shows up as a relatively potent glycine agonist at the NMDA receptor complex site.

Although a number of uncompetitive and competitive NMDA receptor antagonists are already used clinically or are at advanced stages of development, less is known about the therapeutic potential of antagonists at the $glycine_b$ site. Initial preclinical evidence suggests that a different, perhaps more promising, therapeutic profile can be expected from $glycine_b$ antagonism. The $glycine_b$ antagonists have been reported to lack many of the side effects classically associated with NMDA receptor blockade such as: 1) lack of neurodegenerative changes in the cingulate/retrosplenial cortex; 2) lack of psychotomimetic-like effects, and 3) lack of learning impairing effects at anticonvulsive doses. However, more recently some full $glycine_b$ antagonists, have also been reported to have good therapeutic indices following systemic administration as neuroprotective agents in models of focal ischemia; and trauma, as antiepileptics, even in models of partial complex seizures; as anxiolytics; as antipsychotomimetics; in blocking spreading depression; and in models of hyperalgesia.

The compounds of the present invention exhibit no specific affinity for a standard battery of CNS and peripheral receptors, including many subtypes of glutamate receptors. However, they do exhibit affinity at the glycine strychnine-insensitive site of the NMDA receptor complex. For example, utilizing a representative compound, (R)-2-Acetamido-N-benzyl-3-methoxy propionamide, the present inventor has determined that the affinity thereof at the glycine-strychnine-insensitive site of the NMDA receptor complex has a $IC_{50}$ value of 5.3 uM using dichlorokynurenic acid as the ligand. Moreover, other studies have indicated that the proactive effects of this representative compound on threshold extension in rats can be reversed by D-serine, a glycine agonist, in a dose dependent fashion. Thus the compounds of the present invention are believed, without wishing to be bound, to be mediated by its interaction with the $glycine_b$/D-serine site.

However, the compounds of the present invention exhibit little or no side effects caused by non-selective binding with other receptors, particularly the PCP binding site of the NMDA receptor and the glutamate binding site of the NMDA receptor.

There is an endogenous ligand present that binds to the glycine$_b$ site. Some believe that it is glycine, while others believe that it is D-serine. See Snyder, et al., *Am. J. Psychiatry*, 2000, 157, 11 1738–1751; and Baranano, et al.,*Trends in Nurosciences*, 2001, 24, 99–106.

Without wishing to be bound, it is believed that the compounds of the present invention modulate the activity of the glycine$_b$ receptor. Moreover, without wishing to be bound, it is believed that the compounds of the present invention are useful for the treatment of conditions associated with or caused by abnormal receptor activity at the glycine$_b$ receptor site. Without wishing to be bound, it is believed that compounds of the present invention interact with this glycine$_b$ receptor site on the NMDA receptor.

Without wishing to be bound, it is believed that by interacting at the strychnine-insensitive glycine site on the NMDA receptors, the compounds of Formula I are useful in treating or preventing neuronal loss, neurodegenerative diseases and chronic pain. In addition they are also antipsychotics.

Other neurodegenerative diseases which are treated with the compounds of Formula I are Alzheimer's disease, Huntington's disease and Down's syndrome.

The compounds described herein also are useful for treating or preventing dementia.

Besides treating neuropathic pain, the compounds of the present invention find utility in treating or preventing pain, e.g., chronic pain. Such chronic pain can result from surgery, trauma, headache, arthritis, pain associated with a terminal case of cancer, or degenerative diseases. The compounds of Formula I find utility in the treatment of phantom pain that results from amputation of an extremity.

In addition, it is believed, without wishing to be bound, that the strychnine-insensitive glycine site of the NMDA receptors is involved in the development of persistent pain following nerve and tissue injury. Tissue injury, such as that caused by injecting a small amount of formalin subcutaneously into the hindpaw of a test animal, has been shown to produce an immediate increase of glutamate and aspartate in the spinal cord. Without wishing to be bound, it is believed that the administration of the compounds of the present invention reduces the response of spinal cord dorsal horn neurons following formalin injection. These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because the compounds of the present invention block dorsal hormone neuron response induced by subcutaneous formalin injection, they are useful for the treatment of chronic pain, such as pain caused by surgery or by amputation (phantom pain) or by infliction or other wounds The degree of pain is determined by measuring the decrease in the amount of time the animal spends licking the formalin-injected paw after administration of the drug.

Compared to vehicle control, the intraperitoneal injection of the putative glycine receptor modulators of the present invention 30 minutes prior to formalin injection into the hindpaw significantly inhibits formalin-induced chronic pain in a dose-dependent manner as determined by the reduction of the time spent by the mouse licking the formalin injected hindpaw. This is shown in Example 2 hereinbelow.

In the following Examples 1–5, the following were used:
1. Animals

Male or female ICR mice and male or female Long Evans rats provided by animal breeding center of MDS Panlabs Taiwan, Ltd. were used. Space allocation for animals was as follows: 45×23×15 cm for 10 mice, 45×23×15 cm for 6 rats. Mice and rats were housed in APEC® (Allentown Gaging, Allentown, N.J. 08501, U.S.A.) cages in a positive pressure isolator (NuAire®, Mode: Nu-605, airflow velocity 50±5 ft/min, HEPA Filter). All animals were maintained in a controlled temperature (22° C.–24° C.) and humidity (60%–80%) environment with 12 hour light dark cycles for at least one week in MDS Panlabs Taiwan laboratory prior to being used. Free access to standard lab chow for mice and rats (Fwusow Industry Co., Limited, Taiwan) and tap water was granted. All aspects of this work including housing, experimentation and disposal of animals were performed in general accordance with the International Guiding Principles for Biomedical Research Involving Animals (CIOMS Publication No. ISBN 90360194, 1985).

2. Chemicals

The chemicals used were Acetic Acid (Sigma, U.S.A.), Aspirin (ICN Biomedicals Inc.), CGS-19755 (RBI, U.S.A.), Diazepam (Sigma, U.S.A.), Formalin (Wako, Japan), Morphine (National Narcotics Bureau of Taiwan), NMDA (Sigma, U.S.A.), Phenylquionone (Sigma, U.S.A.) and Saline (Astar, Taiwan).

3. (R)-N-Benzyl-3-Acetamido-3-methoxypropionamide was prepared in accordance with the procedure in U.S. Pat. No. 5,773,475. In the following examples, it will be designated as Compound I.

The following experiments illustrate the effectiveness of the compounds in treating pain. In the first series of experiments, a representative compound of the present invention, (R)-2-Acetamido-N-benzyl-3-methoxypropionamide (CMPD I) was utilized at different concentrations.

In the first animal study in Example 1, the degree of pain experienced by the mice after injection by acetic acid is seen by the number of writhes. If the mice experience no pain, there is no writhing. As would be expected, if a pain reliever is not administered to the mice prior to injection of acetic acid, the mice will exhibit writhing.

The protocol is based on the acetic acid writhing test in mice, developed by R. Koster, et al. *Fed. Proc*, 18, 412 (1939), and referred to a Koster test and Hunskarai, S., et al., *J. Neuroscience Meth*. 14: 69–76, 1985.

EXAMPLE 1

Test substance was administered PO (30 or 100 mg/kg) to groups of 3 ICR derived male or female mice weighing 22±2 gms one hour before injection of acetic acid (0.5%, 20 ml/kg IP). Reduction in the number of writhes by 50 percent or more ($\geq$50%) per group of animals observed during the 5 to 10 minute period after acetic acid administration, relative to a vehicle treated control group, indicated analgesic activity.

The results are tabulated hereinbelow:

TABLE 1

Protocol #50390 Analgesia, Acetic Acid Writhing

| Compound | Route | Dose | No. | No. | % Inh. of Writhes |
|---|---|---|---|---|---|
| Distilled water | PO | 20 ml/kg | 1 | 17 | |
| Distilled water | PO | 20 ml/kg | 2 | 12 | |
| Distilled water | PO | 20 ml/kg | 3 | 18 | 0 |
| Distilled water | | | | | |

TABLE 1-continued

Protocol #50390 Analgesia, Acetic Acid Writhing

| Compound | Route | Dose | No. | No. | % Inh. of Writhes |
|---|---|---|---|---|---|
| | | | | | $\bar{x}$ ± SEM 15.7 ± 1.9 |
| Compound I | PO | 100 mg/kg | 1 | 0 | |
| Compound I | PO | 100 mg/kg | 2 | 0 | |
| Compound I | PO | 100 mg/kg | 3 | 0 | 100 |
| | | | | | $\bar{x}$ ± SEM 0 ± 0 |
| Compound I | PO | 30 mg/kg | 1 | 18 | |
| Compound I | PO | 30 mg/kg | 2 | 12 | |
| Compound I | PO | 30 mg/kg | 3 | 15 | 4 |
| | | | | | $\bar{x}$ ± SEM 15 ± 1.7 |
| Aspirin | PO | 100 mg/kg | 1 | 0 | |
| Aspirin | PO | 100 mg/kg | 2 | 0 | |
| Aspirin | PO | 100 mg/kg | 3 | 0 | 100 |
| | | | | | $\bar{x}$ ± SEM 0 ± 0 |

Note: Compound I, at a dose of 100 mg/kg, 3 out of 3 animals showed slight convulsions 15 minutes after oral administration.

As clearly shown, the administration of compound I at 100 mg/Kg was effective in reducing pain, as indicated by the number of writhes. In fact, when compound I was administered at 100 mg/Kg, the mice experienced no writhes after acetic acid administration. The same result was seen with aspirin, a known analgesic.

This next experiment shows that the compounds of the present invention are also effective in reducing pain resulting from tissue injury, such as that caused by injecting a small amount of formalin subcutaneously into the hindpaw of a mouse.

EXAMPLE 2

Test substance was administered (30 or 100 mg/kg) to groups of 5 ICR derived male or female mice weighing 22±2 gms one hour before subplantar injection of formalin (0.02 ml, 5%). Reduction of the induced hind paw licking time recorded during the following 20 to 30 minutes period by 50 percent or more (≧50%) indicated analgesic activity.

The results are tabulated hereinbelow:

TABLE 2

| Compound | Route | Dose | N | Licking Time (sec.) Indiv. | Ave. | % Inh. |
|---|---|---|---|---|---|---|
| Distilled water | PO | 20 ml/kg | 1 | 146 | | |
| Distilled water | PO | 20 ml/kg | 2 | 150 | | |
| Distilled water | PO | 20 ml/kg | 3 | 121 | | |
| Distilled water | PO | 20 ml/kg | 4 | 134 | | |
| Distilled water | PO | 20 ml/kg | 5 | 88 | 128 | 0 |
| Compound I | PO | 100 mg/kg | 1 | 0 | | |
| Compound I | PO | 100 mg/kg | 2 | 0 | | |
| Compound I | PO | 100 mg/kg | 3 | 0 | | |
| Compound I | PO | 100 mg/kg | 4 | 0 | | |
| Compound I | PO | 100 mg/kg | 5 | 0 | 0 | 100 |
| Compound I | PO | 30 mg/kg | 1 | 122 | | |
| Compound I | PO | 30 mg/kg | 2 | 125 | | |
| Compound I | PO | 30 mg/kg | 3 | 62 | | |
| Compound I | PO | 30 mg/kg | 4 | 127 | | |
| Compound I | PO | 30 mg/kg | 5 | 63 | 100 | 22 |
| Aspirin | PO | 300 mg/kg | 1 | 30 | | |
| Aspirin | PO | 300 mg/kg | 2 | 36 | | |
| Aspirin | PO | 300 mg/kg | 3 | 51 | | |

TABLE 2-continued

| Compound | Route | Dose | N | Licking Time (sec.) Indiv. | Ave. | % Inh. |
|---|---|---|---|---|---|---|
| Aspirin | PO | 300 mg/kg | 4 | 9 | | |
| Aspirin | PO | 300 mg/kg | 5 | 54 | 36 | 72 |

Note: Compound I, at a dose of 100 mg/kg, 5 out of 5 animals showed slight convulsions at 15 minutes after oral administration.

The results clearly show that at 100 mg/Kg, there was less licking by the mice than when aspirin was administered at 300 mg/Kg. Therefore, this shows that the compounds of the present invention are more effective than aspirin in reducing pain from tissue damages.

The following example illustrates that the compounds of the present invention are not antagonists of the opioid receptor.

EXAMPLE 3

Groups of 4 male ICR mice weighing 22±2 gms were employed. A dose (30 mg/kg) of test compound dissolved in a vehicle of saline was administered intraperitoneally. The control group received vehicle alone. At pretreatment (0 minute) a focused beam of radiant heat was applied to the middle dorsal surface of the tail to elicit a tail flick response within 6–7.5 seconds in pre-treated animals. A maximum cut-off time of 15 seconds was set. The time required to elicit a pain response was recorded for each animal at 0 and 30 minutes following administration of test compound. Prolongation by 50 percent or more (≧50%) of the time required to elicit a tail flick indicated analgesic activity.

The results are as indicated hereinbelow:

TABLE 3

| Compound | Route | Dose | N | Response Time 0 Min. | 30 Min. | % Inh. |
|---|---|---|---|---|---|---|
| Saline (Vehicle) | IP | 20 ml/kg | 1 | 6.2 | 6.2 | |
| Saline (Vehicle) | IP | 20 ml/kg | 2 | 6.6 | 5.6 | |
| Saline (Vehicle) | IP | 20 ml/kg | 3 | 7.0 | 5.3 | |
| Saline (Vehicle) | IP | 20 ml/kg | 4 | 6.3 | 5.7 | 0 |
| | | | $\bar{x}$ | 6.5 | 5.7 | |
| | | | SEM | 0.2 | 0.2 | |
| Compound I | IP | 30 mg/kg | 1 | 6.4 | 5.8 | |
| Compound I | IP | 30 mg/kg | 2 | 7.3 | 5.0 | |
| Compound I | IP | 30 mg/kg | 3 | 6.4 | 6.0 | |
| Compound I | IP | 30 mg/kg | 4 | 6.5 | 6.2 | 0 |
| | | | $\bar{x}$ | 6.7 | 5.8 | |
| | | | SEM | 0.2 | 0.3 | |
| Morphine | IP | 10 mg/kg | 1 | 7.4 | >15 | |
| Morphine | IP | 10 mg/kg | 2 | 6.5 | >15 | |
| Morphine | IP | 10 mg/kg | 3 | 6.4 | >15 | |
| Morphine | IP | 10 mg/kg | 4 | 7.4 | >15 | 100 |
| | | | $\bar{x}$ | 6.9 | 15.0 | |
| | | | SEM | 0.3 | 0.0 | |

The data show that the radiant heat induced tail flick response was unaffected by administration of the compound at 30 mg/Kg. On the other hand, morphine gave a positive response. This data show that Compound I does not work by the same mechanism as morphine does; i.e., Compound I does not function through an opioid receptor.

The compounds of the present invention do not have affinity for the serotonin 5-$HT_{1A}$ receptor as determined by a challenge with the 5 $HT_{1A}$ agent, 5-methoxy-N,N-dimethyltryptamine, as shown by the following example.

EXAMPLE 4

Test substance was administered PO (30 mg/kg) to a group of 3 Long Evans derived male or female rats weighing 150±20 gms one hour before injection of 5-MeODMT (5-methoxy-N,N-dimethyltryptamine, 3 mg/kg IP). Each animal exhibiting more than 2 head twitches during the ensuing 1 to 5 minute observation period was considered positive. Positive responses occurring in 2 or more (≧2) of the 3 animals was considered a significant effect The results are tabulated hereinbelow:

TABLE 4

| Compound Ave. | Route | Dose | No | Head Twitch | |
|---|---|---|---|---|---|
| Distilled water (Vehicle) | PO | 10 ml/kg | 1 | 0 | |
| Distilled water (Vehicle) | PO | 10 ml/kg | 2 | 0 | |
| Distilled water (Vehicle) | PO | 10 ml/kg | 3 | 0 | 0 |
| Compound I | PO | 30 mg/kg | 1 | 2 | |
| Compound I | PO | 30 mg/kg | 2 | 0 | |
| Compound I | PO | 30 mg/kg | 3 | 0 | 1 |
| Diazepam | PO | 10 mg/kg | 1 | 3 | |
| Diazepam | PO | 10 mg/kg | 2 | 0 | |
| Diazepam | PO | 10 mg/kg | 3 | 2 | 2 |

No potentiation of 5-MeODMT-induced heat twitch was observed utilizing 30 mg/Kg of the representative compound PO.

EXAMPLE 5

Test substance was administered ICVT (intracerebroventricular, 30 μg in 5 μl/mouse). The appearance of convulsions/mortality in 2 or more (≧2) of 3 ICR derived male or female mice weighing 22±2 gms within the 5 minutes thereafter would indicate NMDA receptor agonism. At a dose where no significant agonist activity was seen within 5 minutes, ability to inhibit NMDA (60 mg/kg IV)—induced Tonic convulsions/mortality in 2 or more (≧2) of 3 ICR derived male or female mice weighing 22± gms within the following 5 minutes indicated NMDA receptor antagonist activity.

The results are tabulated hereinbelow:

TABLE 5

| Compound Antagonism | Route | Conc. | N | Agonism | |
|---|---|---|---|---|---|
| Vehicle (Saline) | ICVT | 5 μl/mouse | 3 | 0 | 0 |
| Compound I | ICVT | 30 μg/mouse | 3 | 0 | 1 |
| Cis-4-Phosphono-methyl-2-piperidine-carboxylic acid* | ICVT | 0.2 μg/mouse | 3 | 0 | 3 |
| NMDA | ICVT | 1 μg/mouse | 3 | 3 | — |

*a known potent antagonist at the glutamate site of the NMDA receptor
Note: Compound I, at a dose of 30 μg/mouse, 2 out of 3 animals showed tremors without convulsions after intracerebroventricular administration.

The data indicate that the compounds did not directly inhibit the effects of NMDA activity when 30 ug/mouse was administered intracerebrally.

The results hereinabove in the writhing test further demonstrate that the compounds of the present invention have analgesic activity for the treatment of pain, including inflammatory pain, e.g., rheumatoid arthritis.

EXAMPLE 6

NMDA Induced Hyperalgesia

Holtzman male rats weighing 275 to 325 grams were prepared with lumbar intrathecal catheters under isoflurane anesthesia. The catheters were externalized on the back of the head. Four to five days after implant, the animals were employed.

NMDA administration was accomplished using a gear driven microinjection syringe connected to the spinal catheter by a length of calibrated PE-90 tubing. The catheter plug was immediately replaced to avoid back flow and the rat was replaced in its testing box.

A modified Hargreaves box was used which allows the direction of a focused light beam on the underface of the paw through a glass surface upon which the rat stands. Surface temperature was maintained at 30° C. Withdrawal of the paw was taken as the response. Lack of response within twenty seconds was cause to terminate the test and assign that score.

The rats were placed on the thermal escape box and allowed to acclimate for 30 minutes prior to testing. A measurement was taken for each hindpaw to establish an average baseline latency (counted as time=0). (2R)-2-(acetylamino)-N-[(4-fluorophenyl)methyl]-3-methoxypropanamide solution, that is, test product in this experiment, was given at an intrathecal dose of 1 μg/10 μl 10 minutes prior to intrathecal NMDA. A control group was given an identical amount of saline 10 minutes prior to intrathecal NMDA. Measurements were then made at 15, 30, 60, 120, 240 and 360 minutes after intrathecal NMDA injection. General behavior assessments were made during each period of observation and include: tactile allodynia (vocalization/agitation induced by light touch applied to the body surface), spontaneous vocalization, biting and chewing of body surface, loss of hind limb placing and stepping reflex, loss of hind limb weight bearing and loss of righting reflex.

The saline group (n=2) displayed a hyperalgesic effect with a baseline latency of approximately 1-second dropping to about 7 seconds after about 45 minutes. The test product group (n=2) maintained a normal baseline of about 14 second out to 20 minutes post NMDA injection and then dropping in latency to approximately 10 seconds.

The preliminary data with the NMDA induced thermal hyperalgesic suggest that the 2R-2-(acetylamino)-N-[(4-fluorophenyl)methyl]-3-methoxypropanamide had measurable anti-hyperalgesic actions.

EXAMPLE 7

Sprague Dawley male rats weighing 275 to 325 grams was used in this experiment. In this experiment, the response to neuropathic pain was determined. The neuropathic preparation used to induce an allodynic state is the surgical procedure described by Kim and Chung in *Pain*, 1992, 50,355–363 (1992) and outlined in Chaplain, et al. in *J. Neurosci. Meth.*, 1994, 53, 355–363. Briefly, the left $L_5$ and $L_6$ spinal nerves were isolated adjacent to the vertebral column and ligated with 6-0 silk suture distal to the dorsal root ganglion under isoflurane anesthesia. The rats were allowed a minimum 7 day postoperative recovery period before placement in the study.

Testing groups consisted of 6 rats per group. Each group received test article, (2R)-2-acetyl-amino)-N-[(4- fluorophenyl)methyl]-3-methoxypropanamide (hereinafter "test article"), in one of three concentrations delivered intraperitoneally; the high concentration was 50 mg/kg, the medium concentration was 30 mg/kg and the low concentration was 20 mg/kg. One group of 6 rats received saline control solution at a volume equal to that used for test article.

General behavioral assessments were made during each period of observation and include: tactile allodynia (vocalization/agitation induced by light touch applied to the body surface), spontaneous vocalization, biting and chewing of body surface, loss of hind limb placing and stepping reflex, loss of hind limb weight bearing, and loss of righting reflex. All assessments were noted as "present", "absent" or ranked according to a graded scale.

To assess tactile thresholds, rats were placed in a clear plastic, wire mesh-bottomed cage, divided into individual compartments. Animals were allowed to accommodate and then baseline thresholds were taken prior to drug treatment. To determine the 50% mechanical threshold for paw withdrawal, von Frey hairs were applied to the plantar mid-hindpaw, avoiding the tori (footpads). The eight von Frey hairs used are designated by [log (10*force required to bend hair, mg)] and range from 0.4–15.1 grams. Each hair was pressed perpendicularly against the paw with sufficient force to cause slight bending, and held for approximately 6–8 seconds. A positive response was noted if the paw was sharply withdrawn. Flinching immediately upon removal of the hair was also considered a positive response. Absence of a response ("−") was cause to present the next consecutive stronger stimulus; a positive response ("+") was caused to present the next weaker stimulus. Stimuli were presented successively until either six data points were collected, or the maximum or minimum stimulus was reached. If a minimum stimulus was reached and positive response still occurred, the threshold was assigned an arbitrary minimum value of 0.25 grams; if a maximum stimulus was presented and no response occurred, a maximum threshold value of 15 grams was assigned. If a change in response occurred, either "−" to "+" or "+" to "−", causing a change in the direction of stimulus presentation from descending to ascending or vice-versa, four additional data points were collected subsequent to the change. The resulting pattern of responses were tabulated and the 50% response threshold computer using the formula:

$$\log (\text{threshold, mg} \times 10) = Xf + kh$$

wherein:
Xf=value of the last von Frey hair applied;
k=correction factor based on response pattern (from calibration table)
h=mean distance in log units between stimuli.

Based on observations on normal, -operated rats and sham-operated rats, the cutoff of a 15.1-g hair is selected as the upper limit for testing.

The test was performed to establish an average baseline value, counted as time 0; then again at 15, 30, 60, 120 and 240 minutes after the dosing by the control saline solution or the test article.

The results were as follows:

Four rats were examined at intraperitoneal (IP) doses of 30 to 100 mg/kg.

One rat was given 100 mg/kg of the test article and within 15 minutes the rat was laterally recumbent displaying seizures and bleeding from the nose. The animal was euthanized.

A second rat was given 90 mg/kg of the test article and within 15 minutes the animal became catatonic and unable to right itself. The animal became flaccid and displayed severe exopthalmos. Thirty minutes later there was no change and the animal was euthanized.

A third animal was given 60 mg/kg of the test article and within 15 minutes the animal became catatonic and displayed abnormal ambulation. Severe exopthalmos was also noted. Thirty minutes later, the animal's ambulation appeared worse and it was subsequently euthanized.

A fourth rat was given 50 mg/kg of the test article. The rat appeared slightly catatonic which lasted 60 minutes. No other behavioral deficits were noted.

A fifth rat was given 30 mg/kg of the test article IP and it displayed no behavioral deficit.

Fifteen mg/kg of the test article had previously been shown to have no observable affect.

Using the Chung Model a dose dependent response was seen. The effect lasted approximately 2 hours after injection. Rats given the high dose of 50 mg/kg IP showed a threshold increase from 2 to 11 grams. Behaviorally 6 of 6 rats appeared sedated for approximately 1 hour post injection. No other deficits were noted. Rats given 20 mg and 30 mg/kg test article showed an increase in threshold from approximately 2 to 5 grams. Four of 6 rats given 30 mg appeared sedated for approximately 1 hour. No other deficits were noted. Previous study of 15 mg/kg showed no effect on the Chung Model. Group comparisons using one-way ANOVA performed on maximum effect, area under the curve and on specific time points (15 and 30 minutes post injection) showed no significant difference between groups. The nonparametric Jonckheere Test of ordered alternatives was performed and showed a dose related difference at the $p<0.05$ level.

Test Article delivered intraperitoneally resulted in a significant reversal of tactile allodynia otherwise observed in the Chung model of neuropathy. This model has historically been shown to be affected by a number of clinically relevant agents, such as alpha 2 adrenergic agonists, NMDA receptor antagonists and N-type Ca channel blockers. Importantly, these observations occurred at doses that were believed to be without significant effects upon competing behaviors (e.g., sedation or motor impairment).

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed is:

1. A method for alleviating pain in a patient suffering therefrom comprising administering to said patient an analgesic effective amount of a compound of the formula:

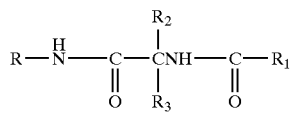

wherein
R is aryl lower alkyl and R is unsubstituted or is substituted with at least one electron withdrawing group or electron donating group;
$R_1$ is lower alkyl and $R_1$ is unsubstituted or substituted with an electron donating group or an electron withdrawing group; and $R_2$ is hydrogen, lower alkyl, lower alkenyl, lower alkynyl, aryl, aryl lower alkyl, halo, heterocyclic, heterocyclic lower alkyl, lower alkyl heterocyclic, lower cycloalkyl, lower cycloalkyl lower alkyl, or ZY;

$R_3$ is lower alkyl, lower alkenyl, lower alkynyl, aryl, aryl lower alkyl, halo, heterocyclic, heterocyclic lower alkyl, lower alkyl heterocyclic, lower cycloalkyl, lower cycloalkyl lower alkyl or ZY;

wherein $R_2$ and $R_3$ may be unsubstituted or substituted with at least one electron withdrawing group or electron donating group and wherein heterocyclic in $R_2$ and $R_3$ is furyl, thienyl, pyrazolyl, pyrrolyl, imidazolyl, indolyl, thiazolyl, oxazolyl, isothiszolyl, isoxazolyl, piperidyl, pyrrolinyl, piperazinyl, quinolyl, triazolyl, tetrazolyl, isoquinolyl, benozofuryl, benzothienyl, morpholinyl, benzoxazolyl, tetrahydrofuryl, pyranyl, indazolyl, purinyl, indolinyl, pyrazolindinyl, imidazolinyl, imidazolindinyl, pyrrolidinyl, furazanyl, N-methylindolyl, methylfuryl, pyridazinyl, pyrimidinyl, pyrazinyl, epoxy, aziridino, oxetanyl or azetidinyl;

Z is O or $NR_6'$;

Y is hydrogen, lower alkyl, aryl, aryl lower alkyl, lower alkenyl, or lower alkynyl, and Y may be unsubstituted or substituted with an electron donating group or an electron withdrawing group, or ZY taken together is $NR_4NR_5R_7$, $NR_4OR_5$, or $ONR_4R_7$;

$R_6'$ is hydrogen or lower alkyl and $R_6'$ maybe unsubstituted or substituted with an electron withdrawing group or electron donating group;

$R_4$ and $R_5$ are independently hydrogen, lower alkyl, aryl, aryl lower alkyl, lower alkenyl, or lower alkynyl, wherein $R_4$ and $R_5$ are independently unsubstituted or substituted with an electron withdrawing group or an electron donating group; and $R_7$ is $COOR_8$, $COR_8$, hydrogen, lower alkyl, aryl, or aryl lower alkyl which $R_7$ maybe unsubstituted or substituted with an electron withdrawing group or electron donating group; and $R_8$ is hydrogen or lower alkyl, or aryl lower alkyl, and the aryl or alkyl group may be unsubstituted or substituted with an electron withdrawing group or an electron donating group;

wherein the electron withdrawing group and electron donating group are selected from the group consisting of halo, nitro, lower alkenyl, lower alkynyl, formyl, aryl, trifluoromethyl, aryl lower alkanoyl, hydroxy, lower alkoxy, lower alkyl, mercapto, lower alkylthio, and lower alkyldithio.

2. The method according to claim 1 wherein $R_2$ is hydrogen.

3. The method according to claim 1 wherein $R_2$ is hydrogen, lower alkyl, aryl, aryl lower alkyl, heterocyclic, heterocyclic lower alkyl, or ZY; and $R_3$ is lower alkyl, aryl, aryl lower alkyl, heterocyclic, heterocyclic lower alkyl or ZY;

wherein $R_2$ and $R_3$ are independently unsubstituted or substituted by an electron withdrawing group or electron donating group.

4. The method according to claim 3 wherein $R_2$ is hydrogen and $R_3$ is lower alkyl, heterocyclic, heterocyclic lower alkyl or ZY;

which $R_3$ may be unsubstituted or substituted with an electron withdrawing group or electron donating group.

5. The method according to claim 1 wherein $R_2$ is hydrogen and $R_3$ is lower alkyl, which may be unsubstituted or substituted with an electron donating or electron withdrawing group or $NR_4OR_5$.

6. The method according to claim 5 wherein $R_3$ is lower alkyl which is unsubstituted substituted with hydroxy or lower alkoxy, or $NR_4OR_5$ or wherein $R_4$ and $R_5$ are independently hydrogen or lower alkyl, R is aryl lower alkyl, which aryl group may be unsubstituted or substituted with an electron withdrawing group and $R_1$ is lower alkyl.

7. The method according to claim 6 wherein aryl is phenyl.

8. The method according to claim 3 wherein one of $R_2$ and $R_3$ is heterocyclic.

9. The method according to claim 8 wherein heterocyclic is heteroaromatic.

10. The method according to claim 8 wherein $R_3$ is furyl, pyridyl, thienyl or thiazolyl.

11. The method according to claim 6 wherein aryl is phenyl and is unsubstituted or substituted with halo.

12. The method according to claim 1 wherein the compound is (R)-N-Benzyl-2-acetamide-3-methoxy-propionamide;
O-methyl-N-acetyl-D-serine-m-fluorobenzylamide;
O-methyl-N-acetyl-D-serine-p-fluorobenzylamide;
N-acetyl-D-phenylglycinebenzylamide;
D-1,2-(N,O-dimethylhydroxylamino)-2-acetamide acetic acid benzylamide; or
D-1,2-(O-methylhydroxylamino)-2-acetamido acetic acid benzylamide.

13. The method according to claim 1 wherein the pain is neuropathic pain.

14. The method according to claim 3 wherein the pain is neuropathic pain.

15. The method according to claim 1 wherein the pain is nociceptive pain.

16. The method according to claim 3 wherein the pain is nociceptive pain.

17. The method according to claim 1 wherein the carbon atom which is substituted by $R_2$ and $R_3$ is in the D configuration.

18. The method of claim 1 wherein the compound is of the formula:

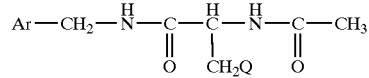

wherein
Ar is aryl which is unsubstituted or substituted with an electron donating or electron withdrawing group, and
Q is lower alkoxy.

19. The method according to claim 18 wherein Ar is unsubstituted aryl or aryl substituted with halo.

20. The method according to claim 18 wherein Q is methoxy.

21. The method according to claim 18 wherein Q is methoxy and Ar is unsubstituted aryl or aryl substituted with halo.

22. The method according to claim 18 wherein the carbon atom which is bonded to $CH_2Q$ is in the D configuration.

23. The method of claim 1 wherein the pain is chronic pain.

24. The method according to claim 3 wherein the pain is chronic pain.

25. The method according to claim 1 wherein R is benzyl which may be unsubstituted or substituted with an electron withdrawing group or electron donating group.

26. The method according to claim 1 wherein $R_1$ is methyl.

27. The method according to claim 1 wherein R is benzyl, $R_1$ is lower alkyl and $R_2$ is hydrogen.

28. The method according to claim 27 wherein $R_3$ is $CH_2Q$, $NR_4OR_5$ or $NR_4NR_5R_7$, wherein Q is lower alkoxy, $R_4$ is hydrogen or alkyl containing 1–3 carbon atoms, $R_5$ is hydrogen or alkyl containing 1–3 carbon atoms and $R_7$ is hydrogen or alkyl containing 1–3 carbon atoms.

29. The method according to claim 28 wherein $R_3$ is $CH_2Q$.

30. The method according to claim 1 wherein $R_1$ is methyl, R is benzyl, $R_2$ is hydrogen, and $R_3$ is $CH_2Q$ wherein Q is methoxy.

31. The method according to claim 1 wherein $R_1$ is methyl, R is m-fluorobenzyl, $R_2$ is H and $R_3$ is $CH_2Q$, wherein Q is methoxy.

32. The method according to claim 1 wherein $R_1$ is methyl, R is p-fluorobenzyl, $R_2$ is H, and $R_3$ is $CH_2Q$ wherein Q is methoxy.

33. The method according to claim 1 wherein $R_1$ is methyl, R is benzyl, $R_2$ is hydrogen and $R_3$ is phenyl.

34. The method according to claim 1 wherein $R_1$ is methyl, R is benzyl, $R_2$ s hydrogen and $R_3$ is $N(CH_3)OCH_3$.

35. The method according to claim 1 wherein $R_1$ is methyl, R is benzyl, $R_2$ is hydrogen and $R_3$ is $NH(OCH_3)$.

36. The method according to claim 1 wherein $R_1$ is methyl, R is fluorophenyl, $R_2$ is H, and $R_3$ is $CH_2Q$, wherein Q is methoxy.

37. A method for alleviating pain in a patient suffering therefrom comprising administering to said patient an analgesic effective amount of a compound of the formula:

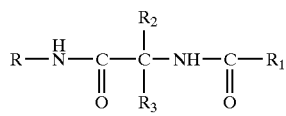

wherein
R is aryl lower alkyl and R is unsubstituted or is substituted with at least one electron withdrawing group or electron donating group selected from the group consisting of halo, nitro, lower alkenyl, lower alkynyl, formyl, aryl, trifluoromethyl, aryl lower alkanoyl, hydroxy, lower alkoxy, lower alkyl, mercapto, lower alkylthio, and lower alkyldithio;

$R_1$ is methyl, and is unsubstituted or substituted with an electron donating group or an electron withdrawing group selected from the group consisting of halo, nitro, lower alkenyl, lower alkynyl, formyl, aryl, trifluoromethyl, lower alkoxy carbonyl, aryl lower alkanoyl, hydroxy, lower alkoxy, lower alkyl, mercapto, lower alkylthio, and lower alkyldithio;

$R_2$ is hydrogen, lower alkyl, lower alkenyl, lower alkynyl, aryl, aryl lower alkyl, halo, heterocyclic, heterocyclic lower alkyl, lower alkyl heterocyclic, lower cycloalkyl, lower cycloalkyl lower alkyl, or ZY;

$R_3$ is lower alkyl, lower alkenyl, lower alkynyl, aryl, aryl lower alkyl, halo, heterocyclic, heterocyclic lower alkyl, lower alkyl heterocyclic, lower cycloalkyl, lower cycloalkyl lower alkyl or ZY;

wherein $R_2$ and $R_3$ may be unsubstituted or substituted with at least one electron withdrawing group or electron donating group and wherein heterocyclic in $R_2$ and $R_3$ is furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrafuryl, pyranyl, indazolyl, purinyl, indolinyl, pyrazolindinyl, imidazolinyl, imidazolindinyl, pyrrolidinyl, furazanyl, N-methylindolyl, methylfuryl, pyridazinyl, pyrimidinyl, pyrazinyl, epoxy, aziridino, oxetanyl or azetidinyl;

Z is O, or $NR_6'$;

Y is hydrogen, lower alkyl, aryl, aryl lower alkyl, lower alkenyl or lower alkynyl, and Y may be unsubstituted or substituted with an electron donating group or an electron withdrawing group, or ZY taken together is $NR_4NR_5R_7$, $NR_4OR_5$, or $ONR_4R_7$;

$R_6'$ is hydrogen or lower alkyl;

$R_4$ and $R_5$ are independently hydrogen, lower alkyl, aryl, aryl lower alkyl, lower alkenyl, or lower alkynyl, and $R_4$ and $R_5$ may be independently unsubstituted or substituted with an electron withdrawing group or an electron donating group; and $R_7$ is $COOR_8$, $COR_8$, hydrogen, lower alkyl, aryl or aryl lower alkyl, which $R_7$ may be unsubstituted or substituted with an electron withdrawing group or electron donating group;

$R_8$ is hydrogen or lower alkyl, or aryl lower alkyl, and the aryl or alkyl group may be unsubstituted or substituted with an electron withdrawing group or an electron donating group.

38. The method according to claim 37 wherein $R_1$ is methyl which is unsubstituted.

39. The method according to claim 37 wherein R is benzyl, which is unsubstituted or substituted on the phenyl ring with an electron donating group or electron withdrawing group.

40. The method according to claim 38 wherein R is benzyl, which is unsubstituted or substituted on the phenyl ring with an electron donating group or electron withdrawing group.

41. The method according to claim 37 wherein $R_2$ is hydrogen.

42. The method according to claim 38 wherein $R_2$ is hydrogen.

43. The method according to claim 39 wherein $R_2$ is hydrogen.

44. The method according to claim 40 wherein $R_2$ is hydrogen.

45. The method according to claim 37 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

46. The method according to claim 38 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl aryl lower alkanoyl, hydroxy, lower alkoxy, lower alkyl, amino, lower alkylamino, dilower alkylamino, aryloxy, mercapto or lower alkylthio.

47. The method according to claim 39 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

48. The method according to claim 40 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

49. The method according to claim 41 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

50. The method according to claim 42 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

51. The method according to claim 43 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl, aryl lower alkanoyl, hydroxy, lower alkoxy, lower alkyl, amino, lower alkylamino, dilower alkylamino, aryloxy, mercapto or lower alkylthio.

52. The method according to claim 44 wherein $R_3$ is a lower alkyl which is unsubstituted or substituted with an electron donating group or electron withdrawing group selected from the group consisting of halo, nitro, carboxy, lower alkenyl, lower alkynyl, formyl, aryl, carboxyamido, trifluoromethyl, lower alkoxycarbonyl,aryl lower alkanoyl, hydroxy, lower alkoxy, lower alkyl, amino, lower alkylamino, dilower alkylamino, aryloxy, mercapto or lower alkylthio.

53. The method according to any one of claims 37–52 wherein $R_3$ is lower alkyl substituted by an electron donating group.

54. The method according to claim 53 wherein $R_3$ is lower alkyl substituted by lower alkoxy.

\* \* \* \* \*